(12) United States Patent
Kohlsaat et al.

(10) Patent No.: US 11,786,363 B2
(45) Date of Patent: Oct. 17, 2023

(54) INJECTOR ASSEMBLY FOR INSERTING AN INTRAOCULAR LENS AND INJECTOR

(71) Applicant: CARL ZEISS MEDITEC AG, Jena (DE)

(72) Inventors: Malte Kohlsaat, Hamburg (DE); Julian Gührs, Quickborn (DE); Niklas Damm, Berlin (DE); Jakob Jastram, Berlin (DE); Alfred Rinman, Hamburg (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 18/001,377

(22) PCT Filed: Jun. 7, 2021

(86) PCT No.: PCT/EP2021/065177
§ 371 (c)(1),
(2) Date: Dec. 9, 2022

(87) PCT Pub. No.: WO2021/249948
PCT Pub. Date: Dec. 16, 2021

(65) Prior Publication Data
US 2023/0190454 A1 Jun. 22, 2023

(30) Foreign Application Priority Data
Jun. 10, 2020 (DE) .................... 10 2020 115 482.8

(51) Int. Cl.
*A61F 2/16* (2006.01)
(52) U.S. Cl.
CPC .................................. *A61F 2/167* (2013.01)

(58) Field of Classification Search
CPC ...... A61F 2/1664; A61F 2/1667; A61F 2/167; A61F 2/1672; A61F 2/1678; A61F 2/1691; A61F 2002/1681
See application file for complete search history.

(56) References Cited

U.S. PATENT DOCUMENTS 11,026,780 B2   6/2021  Maroschek
2003/0212406 A1* 11/2003  Kobayashi ............ A61F 2/1675
                                                        606/107

(Continued)

FOREIGN PATENT DOCUMENTS

EP        2 408 398 B1   6/2014
WO    WO 2012/155887 A1  11/2012

(Continued)

OTHER PUBLICATIONS

Written Opinion of the International Searching Authority for PCT/EP2021/065177 (ISA/CN) dated Aug. 30, 2021 (5 pages).

(Continued)

*Primary Examiner* — Ashley L Fishback
*Assistant Examiner* — Chima U Igboko
(74) *Attorney, Agent, or Firm* — Alston & Bird LLP (57) ABSTRACT

The invention relates to an injector assembly comprising a folding chamber which is designed to receive an intraocular lens having a lens body and two haptics, and comprising a holder, a folding wedge which is attached to the holder and is designed to be introduced into the folding chamber in an insertion direction via a folding chamber opening and to thereby fold the intraocular lens, and two sliders which are each designed to shift one of the two haptics onto the lens body via a shifting of the respective slider out of an initial position and into an end position, wherein at least one of the two sliders has a stop which is designed to abut a component attached to the holder in the initial position of the at least one slider, whereby a movement of the component is blocked (Continued)

and the folding wedge is thereby not permitted to fold the intraocular lens, and said stop is designed to permit the movement of the component in the end position of the at least one slider and the folding wedge is thereby permitted to fold the intraocular lens.

10 Claims, 9 Drawing Sheets

(56) References Cited

U.S. PATENT DOCUMENTS

| | | |
|---|---|---|
| 2009/0043313 A1 | 2/2009 | Ichinohe et al. |
| 2019/0117381 A1 | 4/2019 | Maroscheck et al. |
| 2019/0254812 A1* | 8/2019 | Maroschek ............ A61F 2/1678 |
| 2019/0298512 A1 | 10/2019 | Muchhala et al. |
| 2020/0197169 A1* | 6/2020 | Wu .......................... A61F 2/167 |

FOREIGN PATENT DOCUMENTS

| | | |
|---|---|---|
| WO | WO 2018/006889 A2 | 1/2018 |
| WO | WO 2018/006889 A3 | 1/2018 |

OTHER PUBLICATIONS

Office Action for Australian Patent Application No. 2021288908, dated Jan. 25, 2023 (2 pages).

German Office Action for 10 2020 115 482.8 dated Mar. 26, 2021.

International Search Report and Written Opinion for PCT/EP2021/065177 dated Aug. 30, 2021 (17 pages).

Notice of the Reason for Refusal for Japanese Patent Application No. 2022-576097, dated May 16, 2023 (3 pages).

* cited by examiner

INJECTOR ASSEMBLY FOR INSERTING AN INTRAOCULAR LENS AND INJECTOR

CROSS-REFERENCE TO RELATED APPLICATIONS

The present application is a national phase entry of International Application No. PCT/EP2021/065177, filed Jun. 7, 2021, which claims priority to German Patent Application No. 10 2020 115 482.8, filed Jun. 10, 2020, which are each incorporated herein by reference in their entirety.

The invention relates to an injector assembly for inserting an intraocular lens into the capsular bag of an eye, and to an ophthalmosurgical injector having the injector assembly.

In cataract treatment of an eye, only a small incision is usually made in the cornea of the eye, said incision being large enough to allow a cannula of an injector to be inserted through the incision into the eye. After the incision has been made in the cornea, the lens of the eye is broken up by phacoemulsification and then sucked out of the capsular bag of the eye. Thereafter, an intraocular lens is inserted into the eye by means of the injector. The intraocular lens is folded inside the injector to fit through the cannula. The cannula is inserted into the capsular bag through the incision, and the folded intraocular lens is pushed by the injector through the cannula into the capsular bag, in which the intraocular lens unfolds and thus replaces the original lens. Complications may occur while the intraocular lens is being folded or while the folded intraocular lens is being pushed into the capsular bag. The complications can lead, for example, to the intraocular lens not fully unfolding in the capsular bag or to the intraocular lens even being damaged.

WO 2018/006889 A2 relates to a magazine for an injector system with a folding body for implanting an intraocular lens in an eye. WO 2012/155887 A1 relates to an injector system for implanting an intraocular lens in an eye and to a magazine for the injector system.

It is therefore the object of the invention to provide an injector assembly with which there is a low probability of errors occurring during use of the injector assembly.

The object is achieved by an injector assembly as claimed in independent claim 1. Advantageous developments of the invention are the subject matter of the dependent claims.

The injector assembly according to the invention has: a folding chamber which is designed to accommodate an intraocular lens comprising an optics body and two haptics, a holder, a folding wedge, which is attached to the holder and is designed to be introduced in an insertion direction into the folding chamber via a folding chamber opening and thereby to fold the intraocular lens, and two sliders which are each designed to displace one of the two haptics onto the optics body by displacement of the respective slider from a starting position into an end position, wherein at least one of the two sliders has a stop which is designed to butt against a component attached to the holder in the starting position of the at least one slider, as a result of which a movement of the component is blocked and the folding wedge is thereby not permitted to fold the intraocular lens, and, in the end position of the at least one slider, to permit the movement of the component and to thereby permit the folding wedge to fold the intraocular lens.

By the two haptics being arranged on the optics body by means of the sliders, the haptics are arranged inside the optics body when the intraocular lens is folded by the folding wedge. As a result, the intraocular lens can be introduced into the capsular bag of an eye in a low-error and reproducible manner and the intraocular lens can be unfolded in the capsular bag in a low-error and reproducible manner. Provision of the stop makes it possible to avoid the folding wedge being introduced into the folding chamber before the at least one slider has been brought into the end position and the haptic associated with the at least one slider has thus been pushed onto the optics body. As a result, the injector assembly is particularly low in errors.

It is preferred that the two sliders each have a stop. As a result, the injector assembly has even fewer errors.

It is preferred that the two sliders are arranged at ends of the folding chamber that face away from each other. It is conceivable that the two sliders are arranged at ends of the folding chamber opening that face away from each other.

It is preferred that the component is at least partially formed by the folding wedge. It is particularly preferred that the component is formed entirely by the folding wedge.

The stop is preferably formed by a web which, as seen in the insertion direction, overlaps with the folding chamber opening in the starting position.

It is preferred that the stop is formed by a slider protrusion of the slider protruding from the slider in the direction of the other slider, and the folding wedge has a folding wedge recess, wherein, when, in the end position, the folding wedge is introduced into the folding chamber, the slider protrusion is designed to be arranged in the folding wedge recess, as a result of which the movement of the folding wedge is permitted.

It is preferred that the stop is formed by the slider which has a slider recess which is introduced in a side of the slider that faces the other slider, and the folding wedge has a folding wedge protrusion, which forms the component and when, in the end position, the folding wedge is introduced into the folding chamber, is designed to be arranged in the slider recess, as a result of which the movement of the folding wedge is permitted.

It is preferred that the stop is formed by a slider protrusion of the slider protruding from the slider in a direction counter to the insertion direction, the injector assembly has a protrusion attached to the holder, and the slider protrusion and the folding wedge delimit a recess, wherein the slider protrusion is designed to butt against the folding wedge in the starting position, as a result of which the component is formed by the folding wedge, or to butt against the protrusion, as a result of which the component is formed by the slider protrusion, and when, in the end position, the folding wedge is introduced into the folding chamber, to be arranged in the recess, as a result of which the movement of the folding wedge is permitted.

The component is preferably formed by a protrusion which is attached to the holder and is spatially separated from the folding wedge. The stop is preferably formed by the slider. It is particularly preferred that the stop is formed by a slider protrusion of the slider. It is also conceivable that the slider protrusion protrudes from the slider on a side facing away from the other slider.

It is preferred that the injector assembly has the intraocular lens. It is particularly preferred that the intraocular lens is arranged in the folding chamber.

It is preferred that the two haptics are each C-shaped.

The ophthalmosurgical injector has the injector assembly.

The invention is explained in more detail below with reference to the appended schematic drawings.

As is apparent from FIGS. 1 to 17, an injector assembly 1 has: a folding chamber 8 which is designed to accommodate an intraocular lens 9 comprising an optics body 10 and two haptics 11, a holder 12, a folding wedge 2, which is attached to the holder 12 and is designed to be introduced in an insertion direction 26 into the folding chamber 8 via a folding chamber opening 18 and thereby to fold the intraocular lens 9, and two sliders 3, 4 which are each designed to displace one of the two haptics 11 onto the optics body 10 by displacement of the respective slider 3, 4 from a starting position into an end position, wherein at least one of the two sliders 3, 4 has a stop which is designed to butt against a component attached to the holder 12 in the starting position of the at least one slider 3, 4, as a result of which a movement of the component is blocked and the folding wedge 2 is thereby not permitted to fold the intraocular lens 9, and, in the end position of the at least one slider 3, 4, to permit the movement of the component and to thereby permit the folding wedge 2 to fold the intraocular lens 9. The two sliders 3, 4 are also referred to below as the first slider 3 and the second slider 4. It is both conceivable that only one of the two sliders 3, 4 has the stop, and also conceivable that the two sliders 3, 4 each have a stop. It is conceivable that the stop of the first slider 3 is constructed symmetrically to the stop of the second slider 4. It is conceivable that the two stops are designed to butt against the same component or different components.

Figure 2:
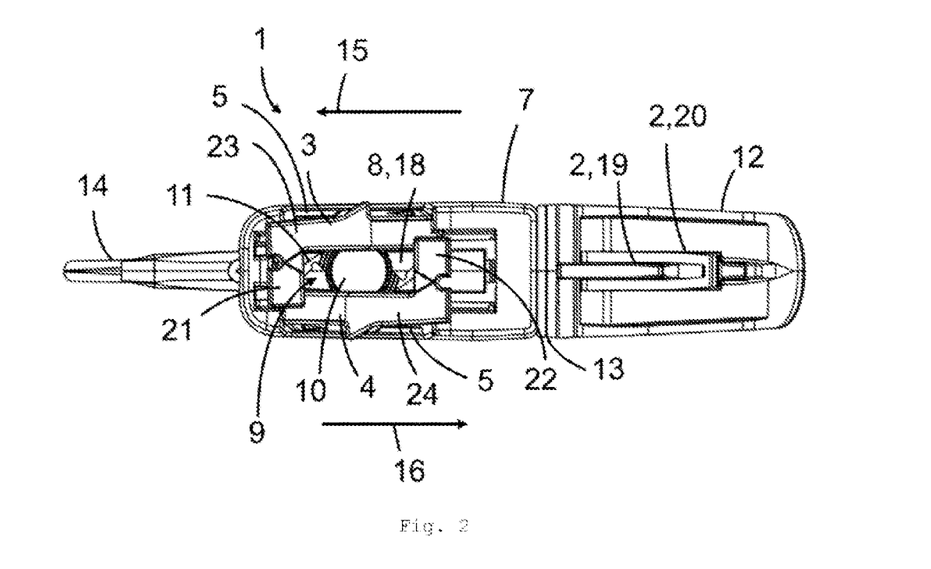
FIG. 2 shows a top view of the injector assembly from FIG. 1.
Figure 14:
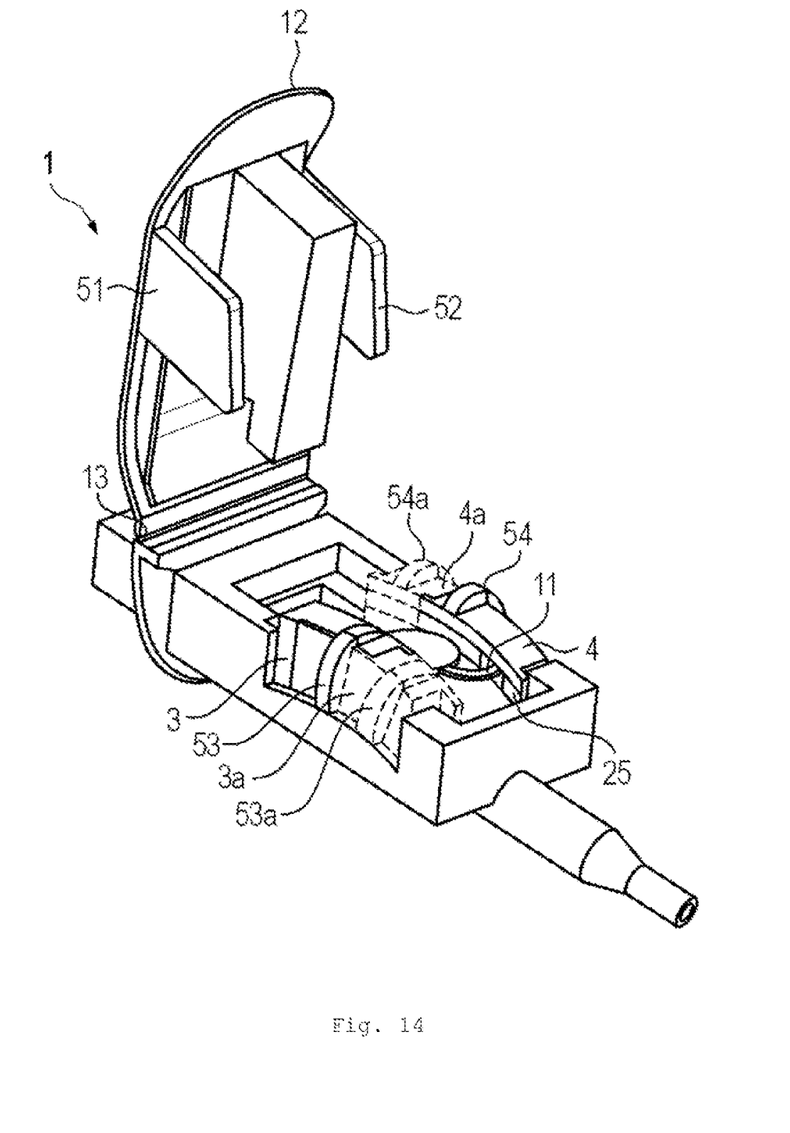
FIG. 14 shows a perspective view of a fifth embodiment of the intraocular lens according to the invention, wherein sliders of the injector arrangement are shown both in a starting position and in an end position.

The injector assembly 1 can have the intraocular lens 9. It is conceivable that the intraocular lens 1 is arranged in the folding chamber 8. FIGS. 2 and 14 in particular show that the two haptics 11 can each be C-shaped.

Figure 1:
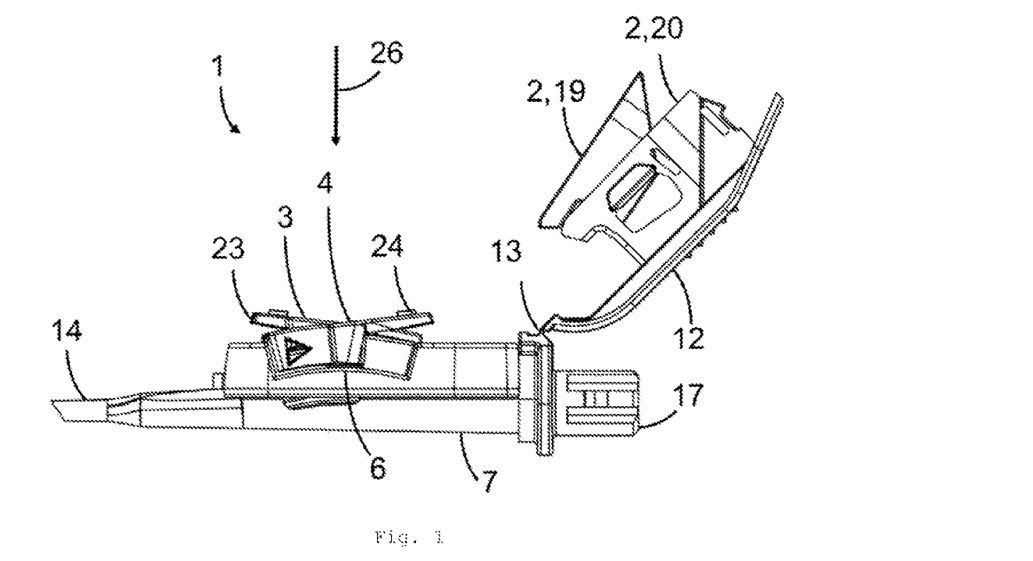
FIG. 1 shows a side view of a first embodiment of the injector assembly according to the invention with sliders, which are shown in a starting position.

FIGS. 1 and 2 in particular show that the two sliders 3, 4 can be arranged at ends of the folding chamber 8 that face away from each other. The ends can be arranged facing away from each other in a direction perpendicular to a displacement direction in which the intraocular lens 9 can be displaced from the folding chamber 8 to a cannula 14 of the injector assembly 1. It can also be seen that the injector assembly 1 can have a first slider track 5 on which the first slider 3 is slidingly mounted and a second slider track on which the second slider 4 is slidingly mounted. The first slider track 5 and the second slider track 6 can be curved such that the sliders 3, 4 cover a curved path when they are displaced from the starting position into the end position. As a result, a collision of the haptics 11 with the peripheral edge of the optics body 10 can be avoided when the haptics 11 are displaced. It can be seen from FIG. 14 that the sliders 3, 4 can each have a slider pin 25 which protrudes from the slider 3, 4 in the direction of the intraocular lens 9. Each of the slider pins 25 is designed to grip one of the two haptics 11 and to displace it onto the optics body 10 when the slider 3, 4 associated with the slider pin 25 is displaced from the starting position into the end position. The slider pins 25 can protrude from a side of the slider 3, 4 which is arranged facing away from the folding wedge 2 arranged outside the folding chamber 8. This ensures that the haptics 11 are displaced to that side of the optics body 10 which faces the folding wedge 2. The effect which can be achieved by this is that the haptics 11 are arranged within the optics body 10 when the folding wedge 2 folds the intraocular lens 9.

It is apparent in particular from FIGS. 1 and 2 that the injector assembly 1 can have an injector body 7, inside which the folding chamber 8 is arranged. The holder 12 can be pivotably attached to the injector body 7 by means of a joint 13. By pivoting of the holder 12 about the joint 13 in the direction of the injector body 7, the folding wedge 2 can be introduced into the folding chamber 8 and the intraocular lens 9 can thereby be folded. The movement of the holder 12 for inserting the folding wedge 2 into the folding chamber 8 is a movement along an arc of a circle, although the insertion direction 26 is indicated as the last section of the movement in FIGS. 1, 3 and 26 by a straight arrow.

For example, FIG. 1 shows that the injector assembly 1 can have an adapter 17 which is designed to be coupled to a plunger in which a stamp is mounted in a longitudinally displaceable manner. It is conceivable that an ophthalmosurgical injector is produced by coupling the injector assembly 1 to the plunger by means of the adapter 17. The ophthalmosurgical injector thus has the injector assembly 1, the plunger and the stamp. The stamp can be designed to be inserted into the folding chamber 8 via the adapter 17 and to push the intraocular lens 9 folded by the folding wedge 2 out of the folding chamber 8 into a cannula 14 of the injector assembly 1 and to push same from the cannula 14 out of the injector assembly 1.

FIGS. 1 and 2 in particular show that the folding wedge 2 has a stationary folding wedge part 20, which is fastened to the holder 12, and a movable folding wedge part 19, which is movably attached to the stationary folding wedge part 20 and can protrude from the stationary folding wedge part 20. The stationary folding wedge part 20 can have a slot in which the movable folding wedge part 19 is arranged. The arrangement with the stationary folding wedge part 20 and the movable folding wedge part 19 can prevent the intraocular lens 9 from slipping away laterally in the direction of the holder 12 and becoming jammed.

Figure 5:
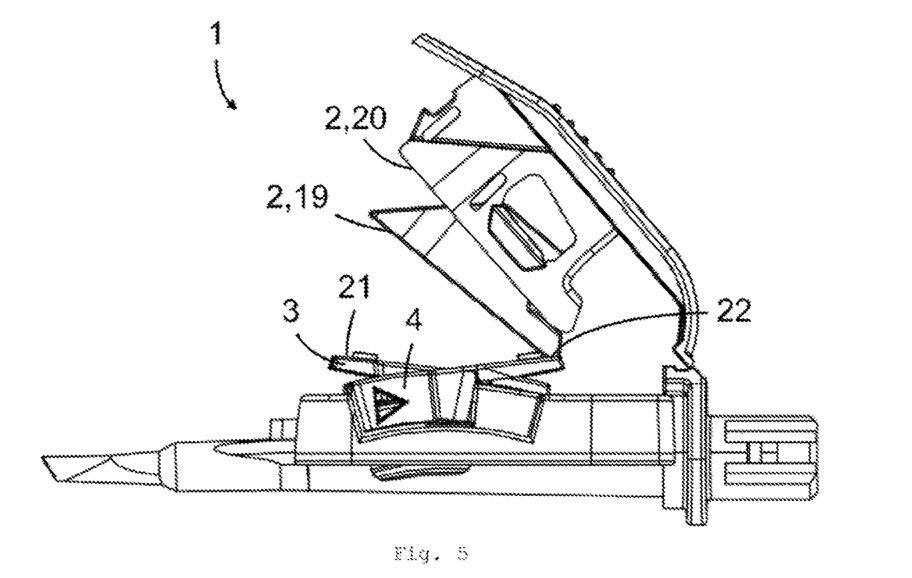
FIG. 5 shows a side view of the first embodiment with the sliders in the starting position, wherein a folding wedge of the injector assembly butts against one of the sliders and thus cannot be introduced into a folding chamber of the injector assembly.
Figure 6:
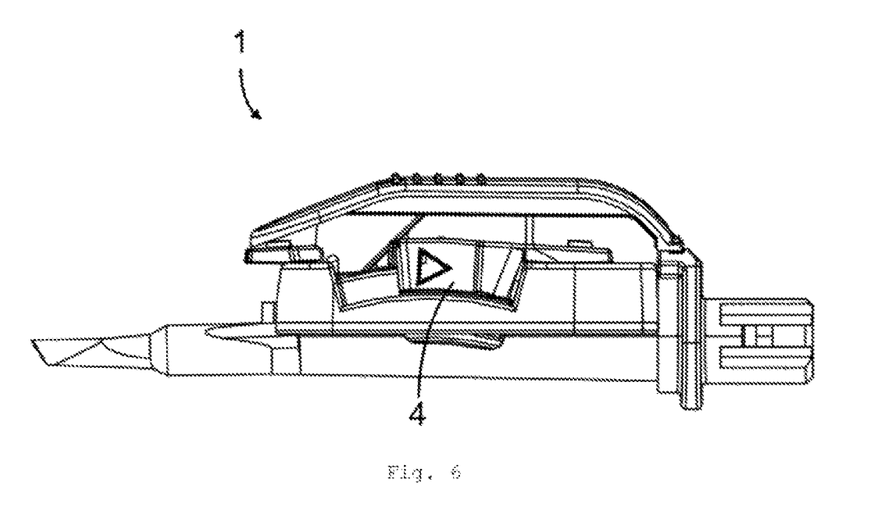
FIG. 6 shows a side view of the first embodiment with the sliders in the end position, wherein the folding wedge is arranged inside the folding chamber.

FIGS. 1 and 6 show a first embodiment of the injector assembly 1. In the first embodiment, the stop is formed by a web 21, 22 which, as seen in the insertion direction 26, overlaps with the folding chamber opening 18 in the starting position. The component is formed at least partially by the folding wedge 2 or is formed entirely by the folding wedge 2. The two sliders 3, 4 can each have a stop. For this purpose, the first slider 3 can have a first web 21 and the second slider 4 can have a second web 22, as is also shown in FIGS. 1 to 6. It is also conceivable that the first slider 3 has a first arm 23 which protrudes from the first slider 3, with the first web 21 protruding from the first arm 23. The first arm 23 can protrude here from the first slider 3 in a first direction of movement 15, in which the first slider 3 is to be displaced from the starting position into the end position. Analogously, it is conceivable that the second slider 4 has a second arm 24 which protrudes from the second slider 4, with the second web 22 protruding from the second arm 24. The second arm 24 can protrude here from the second slider 4 in a second direction of movement 16, in which the second slider 4 is to be displaced from the starting position into the end position. The first arm 23 and/or the second arm 24 can be arranged completely outside the folding chamber opening 18, as seen in the insertion direction 26. The first web 21 and/or the second web 22 can be arranged completely outside the folding chamber 8.

Figure 3:
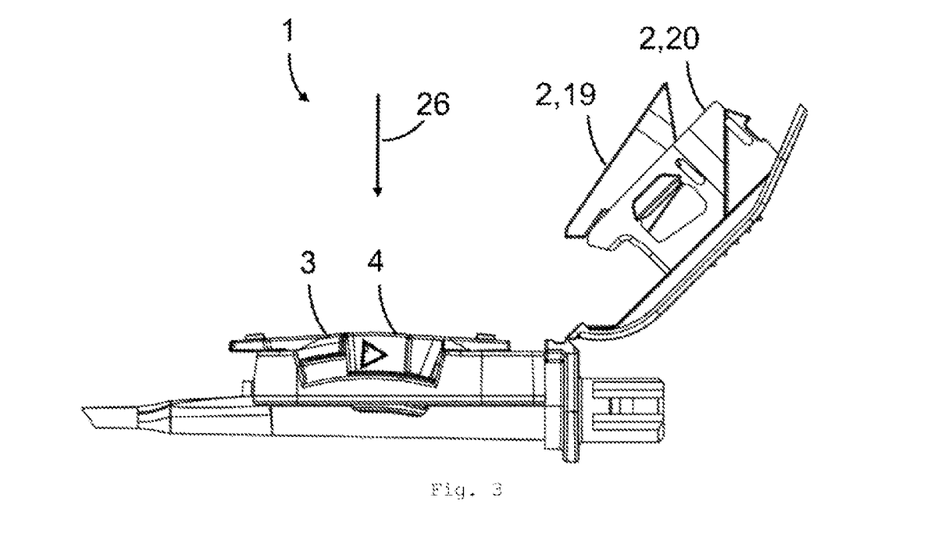
FIG. 3 shows a side view of the first embodiment with the sliders, which are shown in an end position.
Figure 4:
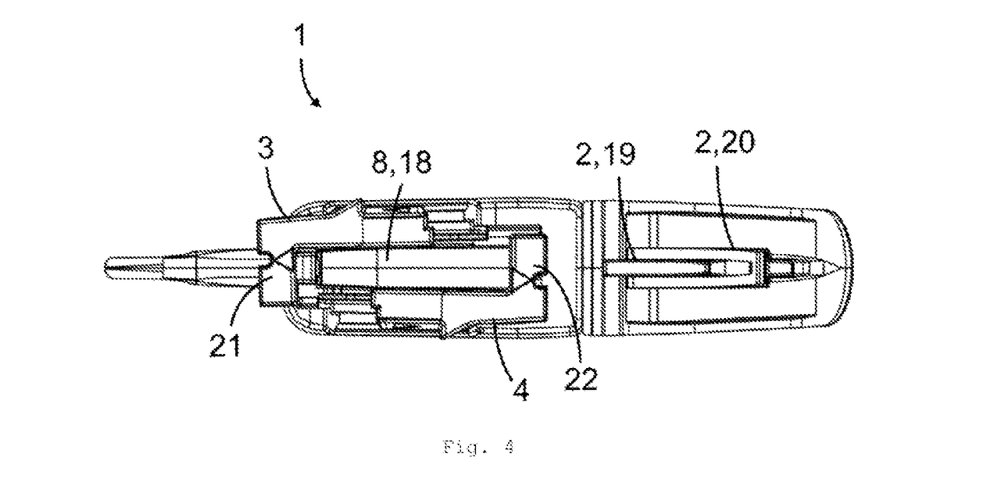
FIG. 4 shows a top view of the injector assembly from FIG. 3.

In FIGS. 1 to 6, the functioning of the injector assembly 1 is illustrated by way of example for the first embodiment. FIG. 1 shows a side view and FIG. 2 a top view of the injector assembly 1, wherein the sliders 3, 4 are arranged in the starting position and the folding wedge 2 is arranged away from the sliders 3, 4. FIG. 3 shows a side view and FIG. 4 shows a top view of the injector assembly 1, wherein the sliders 3, 4 are arranged in the end position and the folding wedge 2 is arranged away from the sliders 3, 4. FIG. 5 shows a side view of the injector assembly 1, wherein the sliders 3, 4 are arranged in the starting position and the folding wedge 2 has been moved starting from FIG. 1 in the direction of the folding chamber 8. In the process, the folding wedge 2 butts against the second web 22. In the event that the first slider 3 is arranged in the starting position and the second slider 4 is arranged in the end position, the folding wedge 2 would butt against the first web 21. FIG. 6 shows a side view of the injector assembly 1, wherein the sliders 3, 4 are arranged in the end position. Here, the folding wedge 2 can be introduced into the folding chamber 8, as is also shown.

Figure 7:
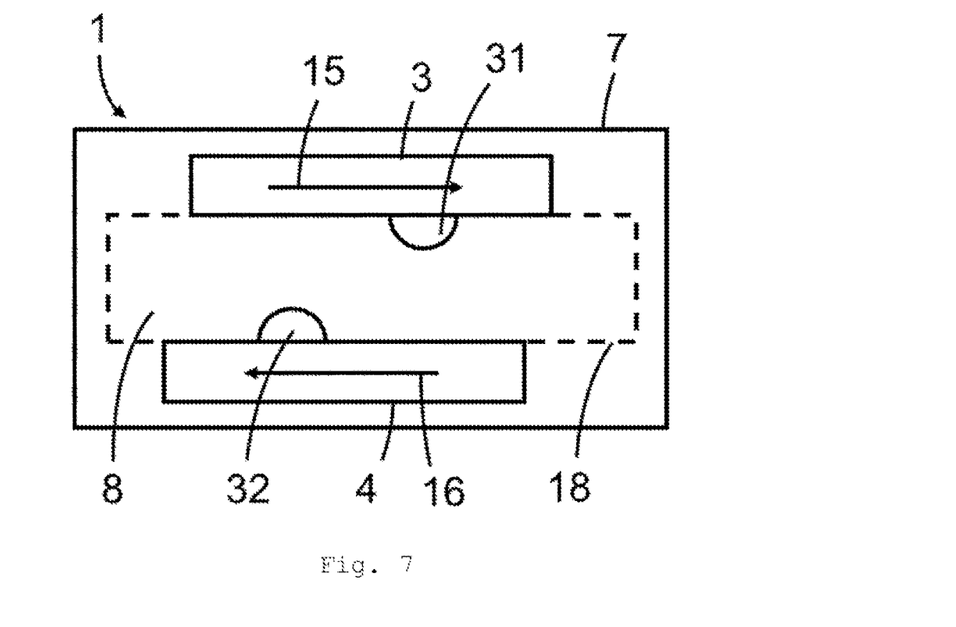
FIG. 7 shows a top view of a second embodiment of the injector assembly according to the invention with sliders, which are shown in a starting position.
Figure 8:
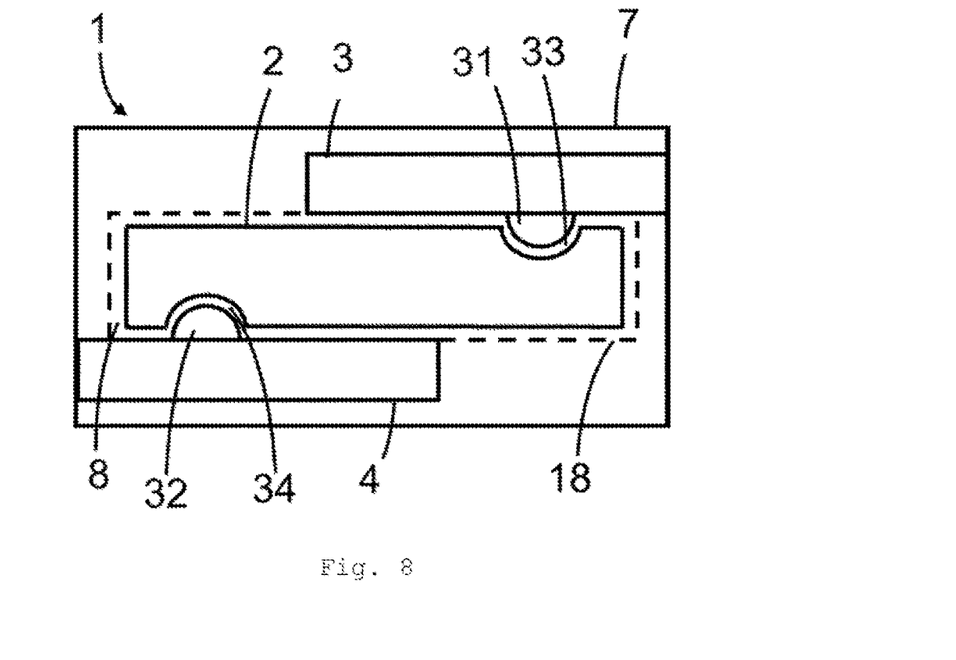
FIG. 8 shows a top view of the second embodiment, wherein the sliders are in an end position and a folding wedge of the injector assembly is arranged inside a folding chamber of the injector assembly.

In FIGS. 7 and 8, a second embodiment of the injector assembly 1 is shown, wherein the stop is formed by a slider protrusion 31, 32 of the slider 3, 4 protruding from the slider 3, 4 in the direction of the other slider 3, 4, and the folding wedge 2 has a folding wedge recess 33, 34, wherein, when, in the end position, the folding wedge 2 is introduced into the folding chamber 8, the slider protrusion 31, 32 is designed to be arranged in the folding wedge recess 33, 34, as a result of which the movement of the folding wedge 2 is permitted. The component is formed at least partially by the folding wedge 2 or is formed entirely by the folding wedge 2. The two sliders 3, 4 can each have a stop. For this purpose, the first slider 3 can have a first slider protrusion 31, the second slider 4 can have a second slider protrusion 32, the folding wedge 2 can have a first folding wedge recess 33 and a second folding wedge recess 34, as is also shown in FIGS. 7 and 8. In this case, the first slider protrusion 31 is designed to engage with the first folding wedge recess 33 and the second slider protrusion 32 is designed to engage with the second folding wedge recess 34. FIG. 7 shows the injector assembly 1 with the sliders 3, 4 in the starting position and without the folding wedge 2, and FIG. 8 shows the injector assembly 1 with the sliders 3, 4 in the end position and with the folding wedge 2 introduced into the folding chamber 8.

Figure 9:
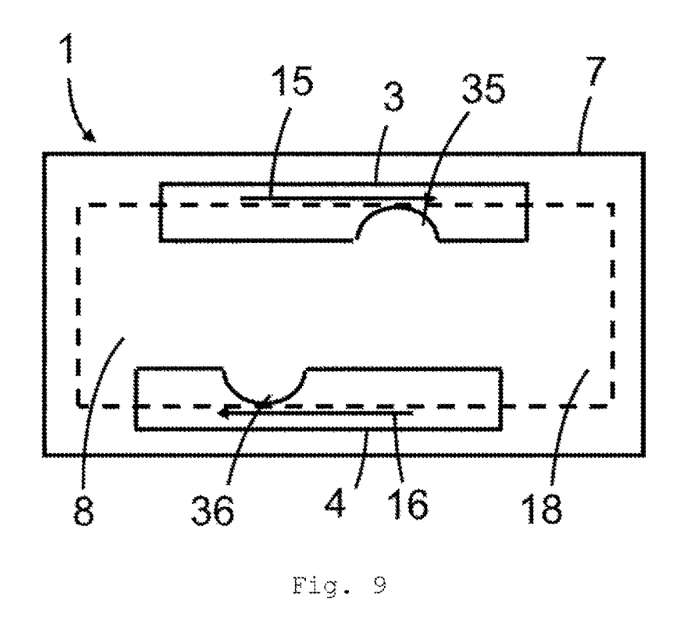
FIG. 9 shows a top view of a third embodiment of the injector assembly according to the invention with sliders, which are in a starting position.
Figure 10:
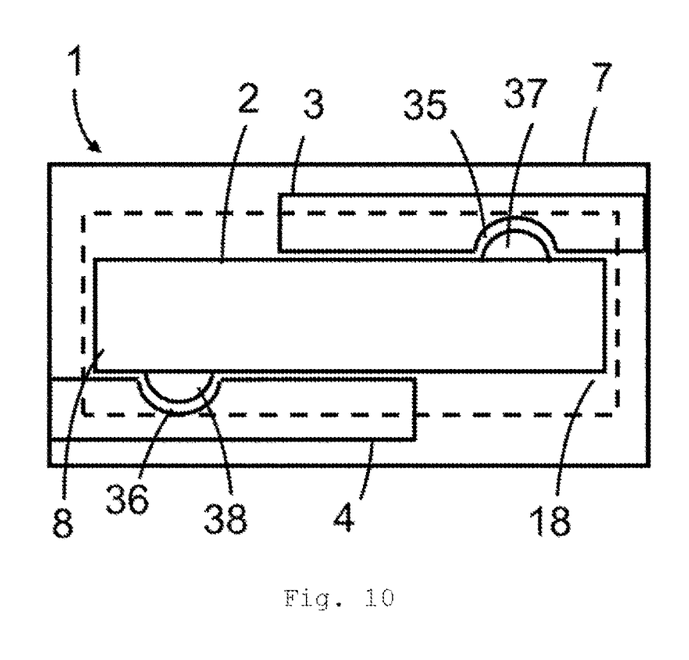
FIG. 10 shows a top view of the third embodiment, wherein the sliders are in an end position and a folding wedge of the injector assembly is arranged inside a folding chamber of the injector assembly.

A third embodiment of the injector assembly 1 is shown in FIGS. 9 and 10, wherein the stop is formed by the slider 3, 4 which has a slider recess 35, 36 which is introduced in a side of the slider 3, 4 that faces the other slider 3, 4, and the folding wedge 2 has a folding wedge protrusion 37, 38, which forms the component and when, in the end position, the folding wedge 2 is introduced into the folding chamber 8, is designed to be arranged in the slider recess 35, 36, as a result of which the movement of the folding wedge 2 is permitted. The component is formed at least partially by the folding wedge 2 or is formed entirely by the folding wedge 2. The two sliders 3, 4 can each be designed as a stop, as is also shown in FIGS. 9 and 10. For this purpose, the first slider 3 can have a first slider recess 35, the second slider 4 can have a second slider recess 36 and the folding wedge 2 can have a first folding wedge protrusion 37 and a second folding wedge protrusion 38. The first folding wedge protrusion 37 here is designed to engage with the first slider recess 35, and the second folding wedge protrusion 38 is designed to engage with the second slider recess 36. FIG. 9 shows the injector assembly 1 with the sliders 3, 4 in the starting position and without the folding wedge 2, and FIG. 10 shows the injector assembly 1 with the sliders 3, 4 in the end position and with the folding wedge 2 introduced into the folding chamber 8.

Figure 11:
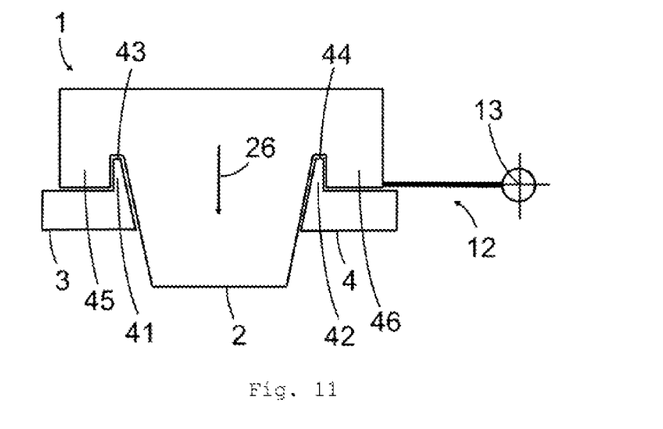
FIG. 11 shows a side view of a fourth embodiment of the intraocular lens according to the invention with sliders which are in an end position and a folding wedge of the injector assembly is arranged inside a folding chamber of the injector assembly.
Figure 12:
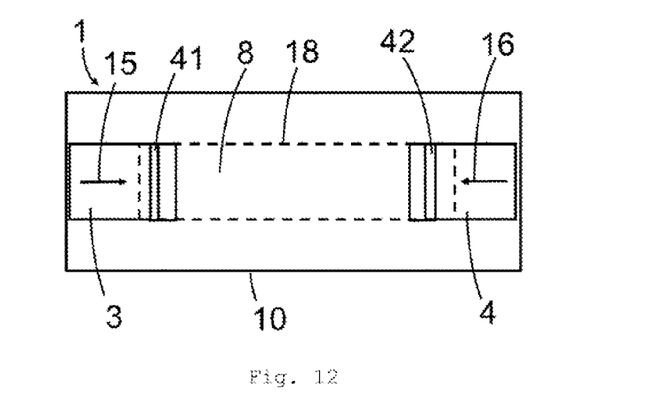
FIG. 12 shows a top view of the fourth embodiment, wherein the sliders are in a starting position.
Figure 13:
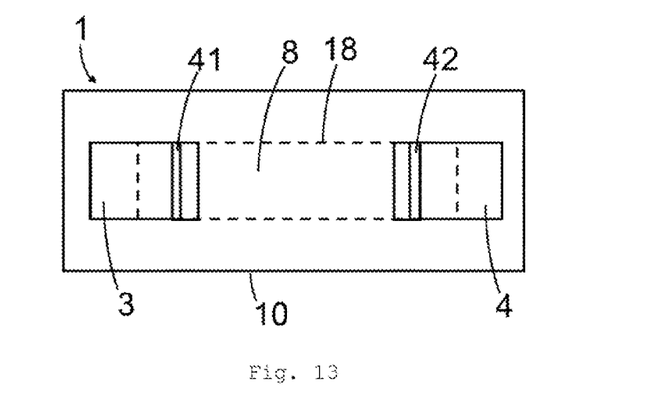
FIG. 13 shows a top view of the fourth embodiment, wherein the sliders are in the end position.

FIGS. 11 to 13 show a fourth embodiment of the injector assembly 1, wherein the stop is formed by a slider protrusion 41, 42 of the slider 3, 4 protruding from the slider 3, 4 in a direction counter to the insertion direction 26, the injector assembly 1 has a protrusion 45, 46 attached to the holder 12, and the slider protrusion 41, 42 and the folding wedge 2 delimit a recess 43, 44, wherein the slider protrusion 41, 42 is designed to butt against the protrusion 45, 46 in the starting position, as a result of which the component is formed by the slider protrusion 41, 42, and when, in the end position, the folding wedge 2 is introduced into the folding chamber 8, to be arranged in the recess 43, 44, as a result of which the movement of the folding wedge 2 is permitted. The two sliders 3, 4 can each be designed as a stop, as is also shown in FIGS. 11 to 13. For this purpose, the first slider 3 can have a first slider protrusion 41, the second slider 4 can have a second slider protrusion 42 and the folding wedge 2 can have a first protrusion 45 and a second protrusion 46. The first protrusion 45 and the folding wedge 2 delimit a first recess 43 and the second protrusion 45 and the folding wedge 2 delimit a second recess 44. In this case, the first slider protrusion 41 is designed to engage with the first recess 43 and the second slider protrusion 42 is designed to engage with the second recess 44, as also shown in FIG. 11. FIGS. 12 and 13 show that a first movement direction 15, in which the first slider 3 is to be moved from the starting position into the end position, is directed toward the second slider 4. In the event that the two sliders 3, 4 are each designed as a stop, a second direction of movement 16, in which the second slider 4 is to be moved from the starting position into the end position, is also directed toward the first slider 3.

Alternatively, it is conceivable that the slider protrusion 41, 42 is designed to butt against the folding wedge 2 in the starting position, as a result of which the component is formed by the folding wedge 2. In this case, a first movement direction 15 in which the first slider 3 is to be moved from the starting position into the end position is directed away from the second slider 4. In the event that the two sliders 3, 4 are each designed as a stop, a second direction of movement 16, in which the second slider 4 is to be moved from the starting position into the end position, is directed away from the first slider 3.

Figure 15:
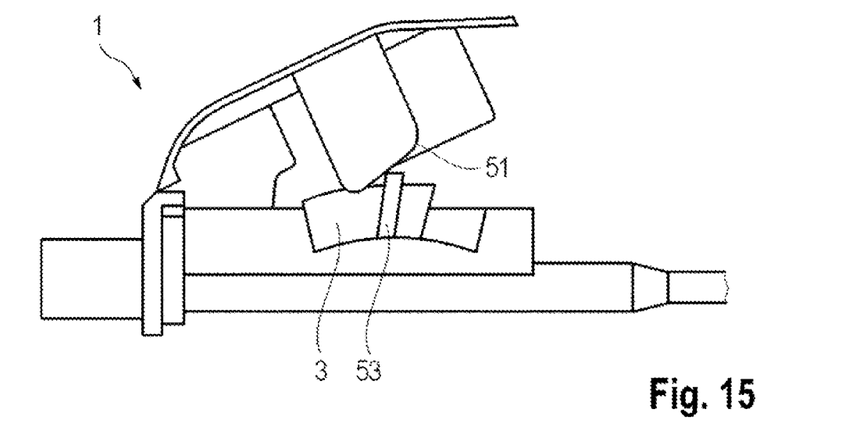
FIG. 15 shows a side view of the fifth embodiment, wherein the sliders are in the starting position.
Figure 16:
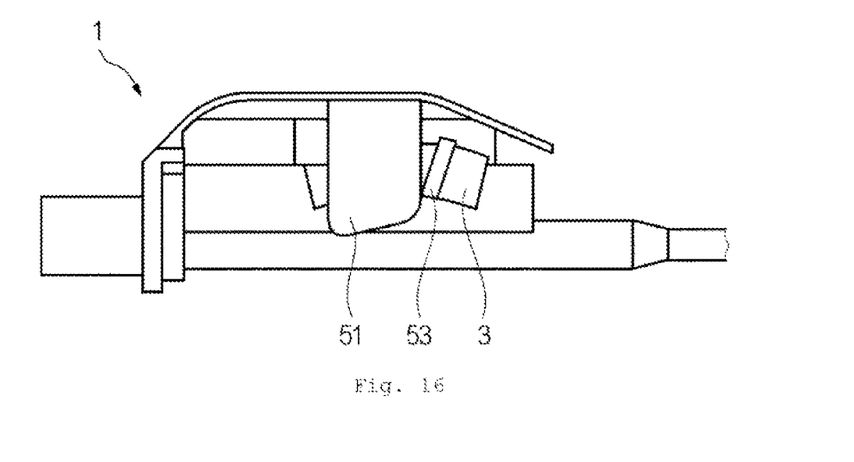
FIG. 16 shows a side view of the fifth embodiment, wherein the sliders are in the end position and a folding wedge of the injector assembly is arranged inside a folding chamber of the injector assembly.

A fifth embodiment of the injector assembly 1 is shown in FIGS. 14 to 16, wherein the component is formed by a protrusion 51, 52 which is attached to the holder 12 and is spatially separated from the folding wedge 2. The stop is formed by a slider protrusion 53, 54 of the slider 3, 4. The two sliders 3, 4 can each be designed as a stop, as is also shown in FIGS. 11 to 13. For this purpose, the first slider 3 can have a first slider protrusion 53, the second slider 4 can have a second slider protrusion 54, and the injector assembly 1 can have a first protrusion 51 and a second protrusion 52 which are each attached to the holder 12. The first slider protrusion 53 can protrude from the first slider 3 on a side facing away from the second slider 4. The second slider protrusion 54 can protrude from the second slider 4 on a side facing away from the first slider 3. The first slider protrusion 53 is designed to butt against the first protrusion 51 in the starting position, and the second slider protrusion 54 is designed to butt against the second protrusion 52 in the starting position. This is illustrated in FIG. 15. By pivoting of the holder 12, the protrusion 51 can butt against the first slider protrusion 53 and the protrusion 52 can butt against the second slider protrusion 54. This makes it possible to shift the first slider 3 from a starting position into an end position. At the same time, this makes it possible to shift the second slider 4 from a starting position into the end position. FIG. 16 shows that the sliders 3, 4 are in the end position and the folding wedge 2 has been introduced into the folding chamber 8. FIG. 14 shows the sliders 3, 4 both in the starting position and in the end position (drawn with dashed lines). The sliders in the starting position have the reference signs 3 and 4 and the associated slider protrusions have the reference signs 53 and 54. The sliders in the end position have the reference signs 3a and 4a and the associated slider protrusions have the reference signs 53a and 54a.

Figure 17:
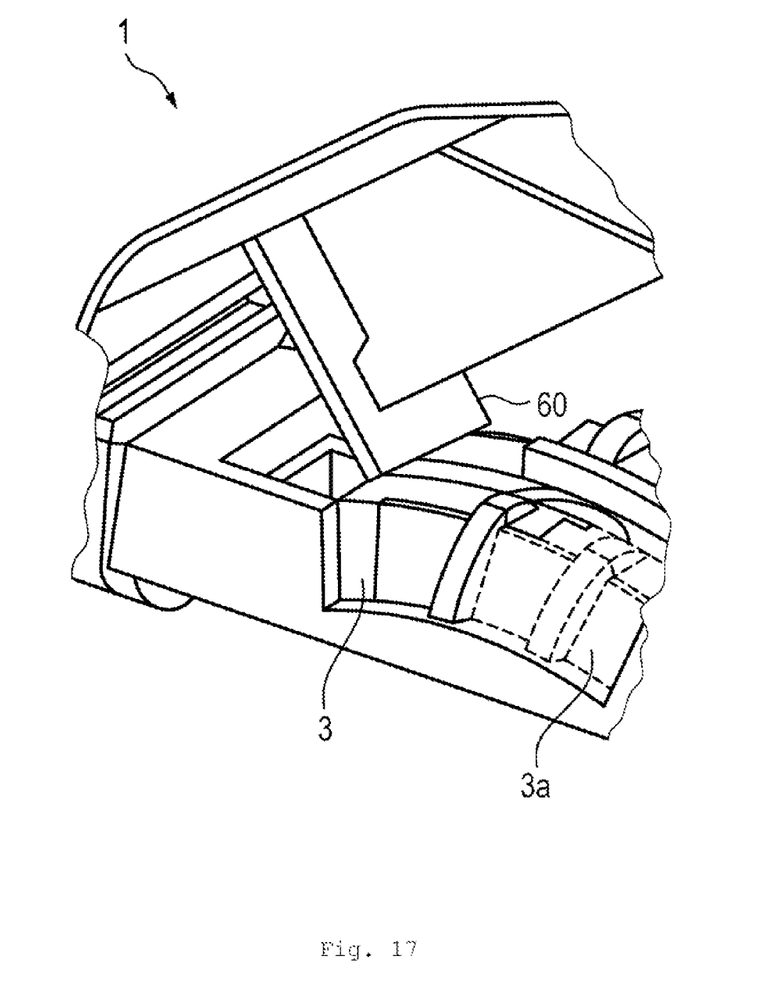
FIG. 17 shows a perspective view of a sixth embodiment of the intraocular lens according to the invention, wherein sliders of the intraocular lens are shown both in a starting position and in an end position.

FIG. 17 shows a sixth embodiment of the injector assembly 1, wherein the component is formed by a protrusion 60 which is attached to the holder 12 and is spatially separated from the folding wedge 2, and the stop is formed by one of the two sliders 3. The slider is shown both in its starting position, denoted by the reference sign 3, and in its end position, denoted by the reference sign 3a (drawn with a dashed line). After pivoting of the holder 12, the protrusion 60 may only penetrate into the injector assembly 1 to an extent such that a ram for conveying an intraocular lens 9 in the direction of the cannula 14 is not impeded.

LIST OF REFERENCE SIGNS 1 injector assembly
2 folding wedge
3 first slider
4 second slider
5 first slider track
6 second slider track
7 injector body
8 folding chamber
9 intraocular lens
10 optics body
11 haptic
12 holder
13 joint
14 cannula
15 first movement direction
16 second movement direction
17 adapter
18 Folding chamber opening
19 movable folding wedge part
20 stationary folding wedge part
21 first web
22 second web
23 first arm
24 second arm
25 slider pin
26 insertion direction
31 first slider protrusion
32 second slider protrusion
33 first folding wedge recess
34 second folding wedge recess
35 first slider recess
36 second slider recess
37 first folding wedge protrusion
38 second folding wedge protrusion
41 first slider protrusion
42 second slider protrusion
43 first recess
44 second recess
45 first protrusion
46 second protrusion
51 first protrusion
52 second protrusion
53 first slider protrusion
54 second slider protrusion
60 protrusion

The invention claimed is:

1. An injector assembly having a folding chamber which is designed to accommodate an intraocular lens comprising an optics body and two haptics, a holder, a folding wedge, which is attached to the holder and is designed to be introduced in an insertion direction into the folding chamber via a folding chamber opening and thereby to fold the intraocular lens-, and two sliders which are each designed to displace one of the two haptics onto the optics body by displacement of the respective slider from a starting position into an end position, wherein at least one of the two sliders has a stop which is designed to butt against a component attached to the holder in the starting position of the at least one slider, as a result of which a movement of the component is blocked and the folding wedge is thereby not permitted to fold the intraocular lens, and, in the end position of the at least one slider, to permit the movement of the component and to thereby permit the folding wedge to fold the intraocular lens.

2. The injector assembly as claimed in claim 1, wherein the component is at least partially formed by the folding wedge-.

3. The injector assembly as claimed in claim 1, wherein the stop is formed by a web which, as seen in the insertion direction, overlaps with the folding chamber opening in the starting position.

4. The injector assembly as claimed in claim 1, wherein the stop is formed by a slider protrusion of the slider protruding from the slider in the direction of the other slider, and the folding wedge has a folding wedge recess, wherein, when, in the end position, the folding wedge is introduced into the folding chamber, the slider protrusion is designed to be arranged in the folding wedge recess, as a result of which the movement of the folding wedge is permitted.

5. The injector assembly as claimed in claim 1, wherein the stop is formed by the slider which has a slider recess which is introduced in a side of the slider that faces the other slider, and the folding wedge has a folding wedge protrusion, which forms the component and when, in the end position, the folding wedge is introduced into the folding chamber, is designed to be arranged in the slider recess, as a result of which the movement of the folding wedge is permitted.

6. The injector assembly as claimed in claim 1, wherein the stop is formed by a slider protrusion of the slider protruding from the slider in a direction counter to the insertion direction, the injector assembly has a protrusion attached to the holder, and the slider protrusion and the folding wedge delimit a recess, wherein the slider protrusion is designed to butt against the folding wedge in the starting position, as a result of which the component is formed by the folding wedge, or to butt against the protrusion, as a result of which the component is formed by the protrusion attached to the holder, and when, in the end position, the folding wedge is introduced into the folding chamber, to be arranged in the recess, as a result of which the movement of the folding wedge is permitted.

7. The injector assembly as claimed in claim 1, wherein the component is formed by a protrusion which is attached to the holder and is spatially separated from the folding wedge.

8. The injector assembly as claimed in claim 7, wherein the stop is formed by the slider.

9. The injector assembly as claimed in claim 8, wherein the stop is formed by a slider protrusion of the slider.

10. An ophthalmosurgical injector having an injector assembly as claimed in claim 1.

* * * * *

UNITED STATES PATENT AND TRADEMARK OFFICE
CERTIFICATE OF CORRECTION

| | |
|---|---|
| PATENT NO. | : 11,786,363 B2 |
| APPLICATION NO. | : 18/001377 |
| DATED | : October 17, 2023 |
| INVENTOR(S) | : Malte Kohlsaat et al. |

It is certified that error appears in the above-identified patent and that said Letters Patent is hereby corrected as shown below:

In the Claims

In Column 8, Line 53, Claim 1, delete "lens-, and" and insert -- lens, and --, therefor.

In Column 8, Line 67, Claim 2, delete "wedge-." and insert -- wedge. --, therefor.

Signed and Sealed this
Twenty-third Day of January, 2024

Katherine Kelly Vidal
*Director of the United States Patent and Trademark Office*